US006214998B1

(12) United States Patent
Decker

(10) Patent No.: US 6,214,998 B1
(45) Date of Patent: Apr. 10, 2001

(54) PROCESS FOR PREPARING 2-CHLORO-5-CHLOROMETHYLTHIAZOLE

(75) Inventor: Matthias Decker, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/507,341

(22) Filed: Feb. 18, 2000

(30) Foreign Application Priority Data

Feb. 26, 1999 (DE) .............................................. 199 08 447

(51) Int. Cl.⁷ .................................................. C07D 277/22
(52) U.S. Cl. ................................................................ 548/202
(58) Field of Search ............................................... 548/202

(56) References Cited

U.S. PATENT DOCUMENTS

| 4,748,243 | 5/1988 | Beck et al. ............................ 548/202 |
| 5,001,138 | 3/1991 | Shiokawa et al. ..................... 514/342 |
| 5,034,404 | 7/1991 | Uneme et al. ......................... 514/365 |
| 5,180,833 | * 1/1993 | Uneme ................................. 548/202 |
| 5,204,360 | 4/1993 | Shiokawa et al. ..................... 514/342 |
| 5,298,507 | 3/1994 | Shiokawa et al. ..................... 514/256 |
| 5,489,603 | 2/1996 | Uneme et al. ......................... 514/365 |
| 5,633,375 | 5/1997 | Uneme et al. ......................... 544/336 |
| 5,679,796 | 10/1997 | Kraatz ................................. 548/202 |
| 5,705,652 | 1/1998 | Jackson et al. ....................... 548/202 |
| 5,811,555 | 9/1998 | Wakasugi et al. .................... 548/202 |
| 5,894,073 | 4/1999 | Matsuda et al. ...................... 548/202 |

FOREIGN PATENT DOCUMENTS

| 196 53 586 | 6/1968 | (DE) . |
| 97/10226 | 3/1997 | (WO) . |
| 97/23469 | 7/1997 | (WO) . |
| 98/32747 | 7/1998 | (WO) . |
| 98/45279 | 10/1998 | (WO) . |

* cited by examiner

Primary Examiner—Robert Gerstl
(74) Attorney, Agent, or Firm—Joseph C. Gil

(57) ABSTRACT

The invention relates to a novel process for preparing 2-chloro-5-chloromethylthiazole by reacting 2-halogenoallyl isothiocyanates with a chlorinating agent.

3 Claims, No Drawings

PROCESS FOR PREPARING 2-CHLORO-5-CHLOROMETHYLTHIAZOLE

The invention relates to a novel process for preparing 2-chloro-5-chloromethylthiazole.

TECHNICAL FIELD OF THE INVENTION

Background of the Invention

It is known that 2-chloro-5-chloromethylthiazole is obtained when allyl isothiocyanate (allyl mustard oil) of the formula (A) is reacted with a chlorinating agent according to the following reaction scheme:

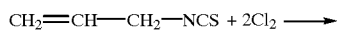

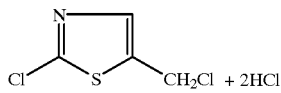

(cf. EP-A 0 260 560).

Furthermore, it is known that 2-chloro-5-chloromethylthiazole can be obtained by reacting allyl isothiocyanates of the formula (B) with a chlorinating agent according to the following reaction scheme:

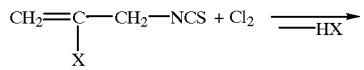

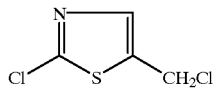

X=leaving group (cf EP-A 0 446 913).

However, these processes have the disadvantage that a substantial excess of chlorinating agent is used, that the processes have to be carried out in highly diluted form and that a high reaction temperature is required.

In addition, the stable intermediate that is formed during the course of the reaction has to be converted exothermally in an additional reaction step into the desired end product. In particular when the process is carried out on an industrial scale, this involves additional cost for controlling the reaction.

Furthermore, EP 0 763 531, EP 0 794 180 and WO 98/45279 describe the chlorination of 3-chloroallyl isothiocyanate.

These processes have the disadvantage that byproducts are formed which necessitate expensive purification by distillation or recrystallization.

In principle, other processes for preparing 2-chloro-5-chloromethylthiazole have been described in WO 97/10226, EP 0 775 700, EP 0 780 384, WO 97/23469, WO 98/32747 and DE 196 53 586.

These processes have the disadvantages that, on the one hand, they use, as starting materials, compounds which are difficult to obtain and that, on the other hand, they give poor yields and in some cases involve complicated purification processes or reactions with low conversion.

DETAILED DESCRIPTION OF THE INVENTION

It has now been found that 2-chloro-5-chloromethylthiazole of the formula (1)

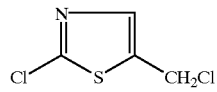

is obtained in good yields and with high purity when 2-halogeno-allyl isothiocyanate of the formula (II)

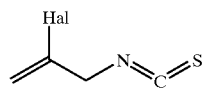

in which
Hal represents chlorine or bromine
is reacted with a chlorinating agent in the presence of a dipolar aprotic diluent at low temperatures.

Surprisingly, the process according to the invention affords 2-chloro-5-chloromethylthiazole of the formula (1) in very good yields and in such high purity that the resulting crude solution can be employed directly for subsequent reactions (preparation of insecticides, see EP-A 0 192 060).

Surprisingly, the process can be carried out successfully at low temperatures, even though the prior art (EP-A 0 446 913) describes, for a similar process at low temperatures, the termination of the reaction at an intermediate stage.

Using the process according to the invention therefore reduces the costs of controlling the reaction, since the reaction can be carried out in one step and at low temperatures. Moreover, costly purification of the product can be dispensed with, since it is obtained in very high purity and can be employed directly for subsequent reactions.

Using, for example, 2-chloroallyl isothiocyanate as starting material and elemental chlorine as chlorinating agent, the course of the reaction of the process according to the invention can be illustrated by the following formula scheme:

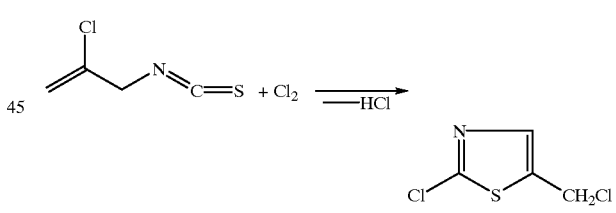

The formula (II) provides a general definition of the 2-halogenoallyl isothiocyanates to be used as starting materials in the process according to the invention. In the formula (II), Hal preferably represents chlorine or bromine.

The 2-halogenoallyl isothiocyanates are generally known or can be prepared by known methods (see EP-A 0 446 913).

Suitable chlorinating agents are elemental chlorine and compounds which give off chlorine under the reaction conditions, such as, for example, sulphuryl chloride or phosgene. The starting material is reacted with from 0.8 to 2 equivalents, preferably from 1.0 to 1.5 equivalents, particularly preferably from 1.15 to 1.40 equivalents, of the chlorinating agent.

The process according to the invention is carried out in the presence of a dipolar aprotic solvent, preferably acetonitrile, dimethylformamide, dimethyl sulphoxide, in particular acetonitrile.

A ratio of from 1 to 20 parts, preferably from 2 to 4 parts, of solvent per part of starting material is employed here.

When carrying out the process according to the invention, the reaction temperatures can be varied within a relatively wide range. In general, the process is carried out at temperatures between −70° C. and 25° C., preferably at temperatures between −10° C. and 20° C., in particular at from 10° to 15° C.

The reaction can also be carried out under reduced or elevated pressure, but it is preferably carried out under atmospheric pressure.

Additional stirring at 20° C. and degassing of the reaction solution already gives a solution of 2-chloro5-chloromethylthiazole which contains only a few other remaining components (after the solvent fraction has been stripped off, the product is present in a purity of from 92 to 94%).

It is therefore possible to employ this solution directly for the subsequent reactions in the synthesis in question of active compound.

Due to the high purity of the 2-chloro-5-chloromethylthiazole in the reaction mixture, isolation is likewise easy.

After cooling the reaction mixture to from −10° C. to −50° C., preferably to from −15° C. to −20° C., 2-chloro-5-chloromethylthiazole hydrochloride crystallizes out and can be filtered off. The crystals are washed with cold solvent and, by addition of water at from 20° C. to 50° C., preferably at from 30° C. to 40° C., 2-chloro-5-chloromethylthiazole is liberated and can separated off as lower liquid phase.

Washing with more water and drying of the organic phase gives 2-chloro-5-chloromethylthiazole in a good yield and high purity (94% pure product in a yield of 71%).

An alternative work-up possibility comprises degassing the reaction mixture under gentle conditions (30° to 40° C., 20 to 200 mbar), distilling off the solvent and washing the distillation residue with water to remove the solvents and residual acid.

If, instead of a chlorinating agent, an appropriate brominating agent is employed in the process according to the invention, 2-bromo5-bromomethylthiazole of the formula (III)

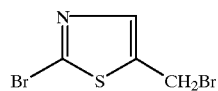

(III)

is obtained.

2-bromo-5-bromomethylthiazole of the formula (E) is known (cf EP-A 0 376 279).

The 2-chloro-5-chloromethylthiazole of the formula (I) to be prepared by the process according to the invention can be employed as intermediate for preparing biologically active compounds, for example insecticides (cf., for example EP-A 0 192 060).

PREPARATION EXAMPLES

EXAMPLE 1

580 g (4.0 mol) of 2-chloroallyl isothiocyanate are dissolved in 860 g of acetonitrile. At from 10° to 15° C., 390 g (5.5 mol) of chlorine are introduced, and the mixture is stirred at from 20° to 25° C. for 2 hours. The mixture is cooled to −10° C. and stirred at this temperature for one hour. The resulting crystals are washed with cold acetonitrile.

The crystals are admixed with 2 kg of water having a temperature of 40° C., resulting in the formation of two liquid phases. The phases are separated and the organic phase is washed with 400 g of water at from 30° to 35° C. and dried under reduced pressure at 30° C.

This gives 507 g (2.84 mol) of 2-chloro-5-chloromethylthiazole as a melt having a content of 94% (GC, internal standard); this corresponds to a yield of 71% of theory.

EXAMPLE 2

560 g (4.0 mol) of 2-chloroallyl isothiocyanate are reacted as in Example 1. After the reaction, the mixture is stirred at from 20° to 25° C. for two hours. The mixture is subsequently degassed under reduced pressure at from 30° to 35° C.

This gives 1838 g of a 34% strength (GC, internal standard) solution of 2-chloro-5-chloromethylthiazole in acetonitrile; this corresponds to a yield of 93% of theory.

After the solvent faction has been stripped off, the product has a purity of 96%.

EXAMPLE 3

560 g (4.0 mol) of 2-chloroallyl isothiocyanate are reacted as in Example 1. After the mixture has been stirred at from 20° to 25° C. for two hours, most of the acetonitrile, about 750 g, are distilled off under reduced pressure at from 30° to 35° C.

At from 30° to 35° C., the residue is admixed with 41 of water, the phases are separated and the organic phase is washed with 400 g of water and dried under reduced pressure at 30° C.

This gives 635 g of 2chloro-5-chloromethylthiazole in a purity of 92% (GC, internal standard), corresponding to a yield of 87% of theory.

What is claimed is:

1. A process for preparing a 2-chloro-5-chloromethylthiazole of the formula (I)

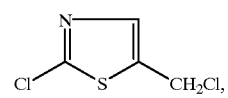

(I)

comprising the step of reacting a 2-halogenoallyl isothiocyanate of the formula (II)

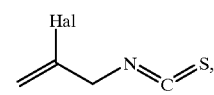

(II)

wherein

Hal represents bromine or chlorine with a chlorinating agent in the presence of a dipolar aprotic solvent.

2. The process of claim 1, wherein said chlorinating agent is selected from the group consisting of chlorine, sulphuryl chloride and phosgene.

3. The process of claim 1, wherein said dipolar aprotic solvent is selected from the group consisting of acetonitrile, dimethylformamide and dimethyl sulfoxide.

* * * * *